US012682987B2

(12) United States Patent
Langevin

(10) Patent No.: US 12,682,987 B2
(45) Date of Patent: Jul. 14, 2026

(54) MOLECULAR DESIGN USING LOCAL EXPLORATION

(71) Applicants: Sanofi, Paris (FR); Ecole Normale Superieure, Paris (FR); Sorbonne Universite, Paris (FR); Centre National de la Recherche Scientifique, Paris Cedex (FR)

(72) Inventor: Maxime Langevin, Paris (FR)

(73) Assignee: Sanofi, Paris (FR)

( * ) Notice: Subject to any disclaimer, the term of this patent is extended or adjusted under 35 U.S.C. 154(b) by 368 days.

(21) Appl. No.: 18/274,057

(22) PCT Filed: Jan. 27, 2022

(86) PCT No.: PCT/EP2022/051953
§ 371 (c)(1),
(2) Date: Jul. 25, 2023

(87) PCT Pub. No.: WO2022/162094
PCT Pub. Date: Aug. 4, 2022

(65) Prior Publication Data
US 2024/0428897 A1      Dec. 26, 2024

(30) Foreign Application Priority Data
Jan. 27, 2021    (EP) ..................................... 21315009

(51) Int. Cl.
*G16C 20/50* (2019.01)
*G16C 20/70* (2019.01)
(52) U.S. Cl.
CPC ............. *G16C 20/50* (2019.02); *G16C 20/70* (2019.02)
(58) Field of Classification Search
CPC ........ G16C 20/50; G16C 20/70; G16C 20/30; G06N 3/044; G06N 3/084; G06N 3/0442;
(Continued)

(56) References Cited

U.S. PATENT DOCUMENTS

2003/0229477 A1    12/2003   Schurer et al.
2019/0325983 A1*   10/2019   Tagade ................... G16C 20/70
(Continued)

FOREIGN PATENT DOCUMENTS

WO     WO-2020016579 A2 *  1/2020   ............. G16C 20/70
WO     WO-2021152414 A1 *  8/2021   ............. G16C 20/80
(Continued)

OTHER PUBLICATIONS

Arus-Pous et al., "Smiles-based deep generative scaffold decorator for de-novo drug design," Journal of Cheminformatics, May 29, 2020, 12:38.

(Continued)

*Primary Examiner* — Jeffrey P Aiello
(74) *Attorney, Agent, or Firm* — Fish & Richardson P.C.

(57)      ABSTRACT

Systems and methods for generating potential medicinal molecules using memory networks are descried. A method for generating analogs of a molecule includes: receiving one or more initial molecular structures; generating one or more of token string representations for each of the one or more initial molecular structures, each token string representation corresponding to an analog of a corresponding initial molecular structure. Generating the token string representations of analogs includes, for each further token string representation: sequentially processing a token string representation of a substructure of the corresponding initial molecular structure using a memory network; and subsequent to processing the token string representation of a substructure, sampling one or more additional tokens using the memory network. The token string representations each comprise a plurality of tokens representing predefined structures of a molecule. The memory network encodes a sequential probability distribution on the tokens using an internal state of the memory network.

20 Claims, 7 Drawing Sheets

(58) Field of Classification Search

CPC ........ G06N 3/0475; G06N 3/09; G06N 3/092; G06N 3/02; G06N 3/04; G06N 3/002; G06N 3/00; G06N 3/091; G06N 3/08; G06N 3/042; G06N 3/082; G06N 20/00; G06N 7/01; G06F 18/2178

USPC .......... 382/128; 702/22, 27, 19, 30, 189, 23, 702/181, 127, 32, 188; 703/11, 2, 12, 1; 706/128, 45, 12, 52, 924

See application file for complete search history.

(56) References Cited

U.S. PATENT DOCUMENTS

| | | | |
|---|---|---|---|
| 2020/0272702 A1* | 8/2020 | Takeda | G06N 3/09 |
| 2022/0108765 A1* | 4/2022 | Teshima | G06N 3/0442 |
| 2022/0189578 A1* | 6/2022 | Takeda | G06N 3/047 |
| 2023/0075100 A1* | 3/2023 | Zavoronkovs | G06N 3/045 |

FOREIGN PATENT DOCUMENTS

| | | |
|---|---|---|
| WO | WO 2022/043362 | 3/2022 |
| WO | WO 2022/162094 | 8/2022 |

OTHER PUBLICATIONS

Gupta et al., "Generative Recurrent Networks for De Novo Drug Design," Molecular Informatics, Jan. 2018, 37(1-2):1700111.

Handbook of Chemoinformatics: From Data to Knowledge in 4 Volumes, Gasteiger (ed.), Aug. 8, 2023, "Chapter 11.3: Smiles—A Language for Molecules and Reactions", Weininger, pp. 80-102.

International Preliminary Report on Patentability in International Appln. No. PCT/EP2022/051953, mailed on Aug. 10, 2023, 8 pages.

International Search Report and Written Opinion in International Appln. No. PCT/EP2022/051953, mailed on May 13, 2022, 11 pages.

Langevin et al., "Scaffold-Constrained Molecular Generation," Journal of Chemical Information and Modeling, Dec. 10, 2020, 60(12):5637-5646.

Langevin et al., "Supporting Information: Scaffold-Constrained Molecular Generation," Journal of Chemical Information and Modeling, Dec. 10, 2020, pp. S1-S15.

Segler et al., "Generating Focused Molecule Libraries for Drug Discovery with Recurrent Neural Networks," ACS Cent. Sci., Dec. 28, 2017, pp. 4, 1, 120-131.

* cited by examiner

Receive one or more initial molecular structures 4.1

Figure 4:
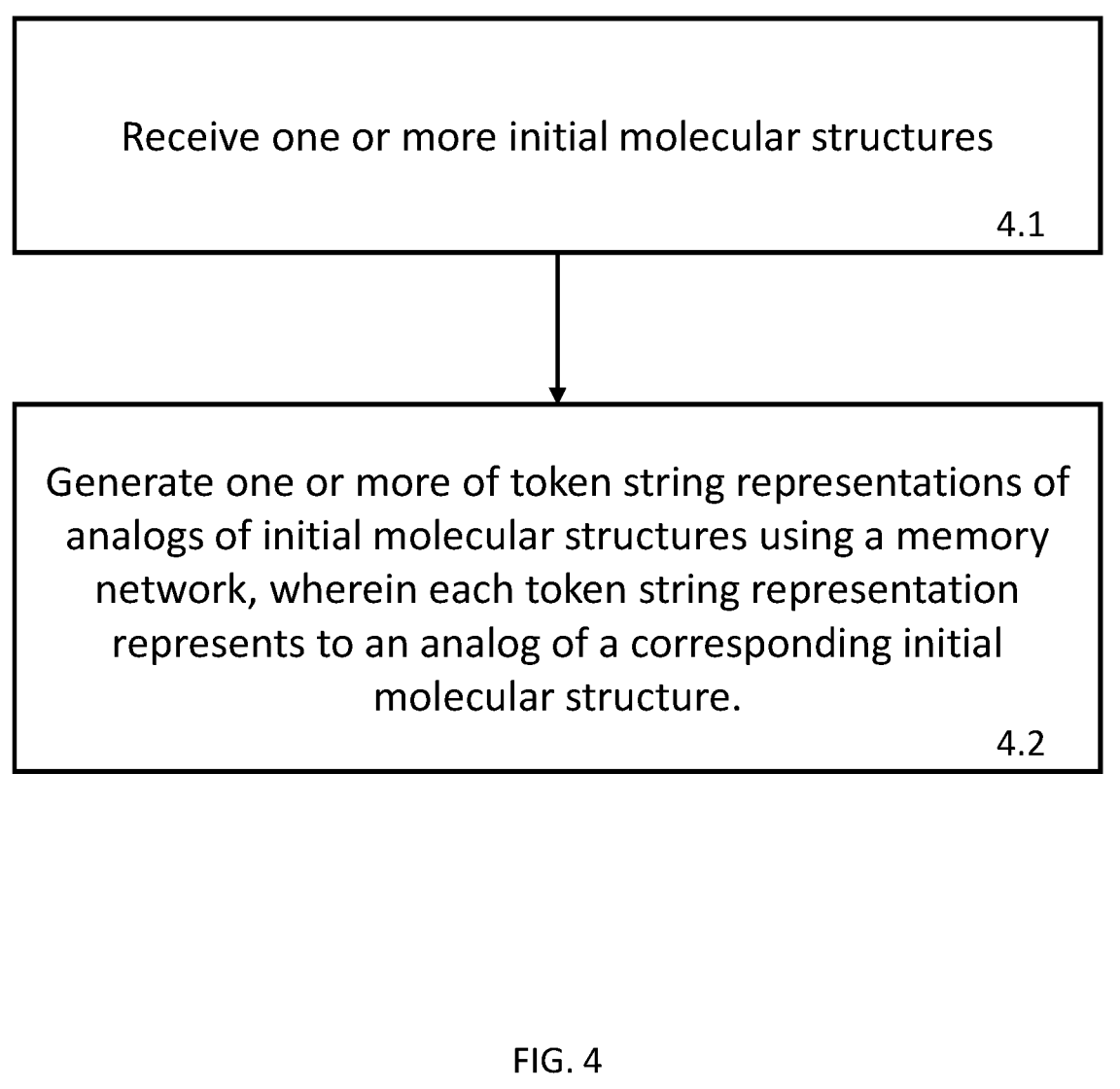

Generate one or more of token string representations of analogs of initial molecular structures using a memory network, wherein each token string representation represents to an analog of a corresponding initial molecular structure.

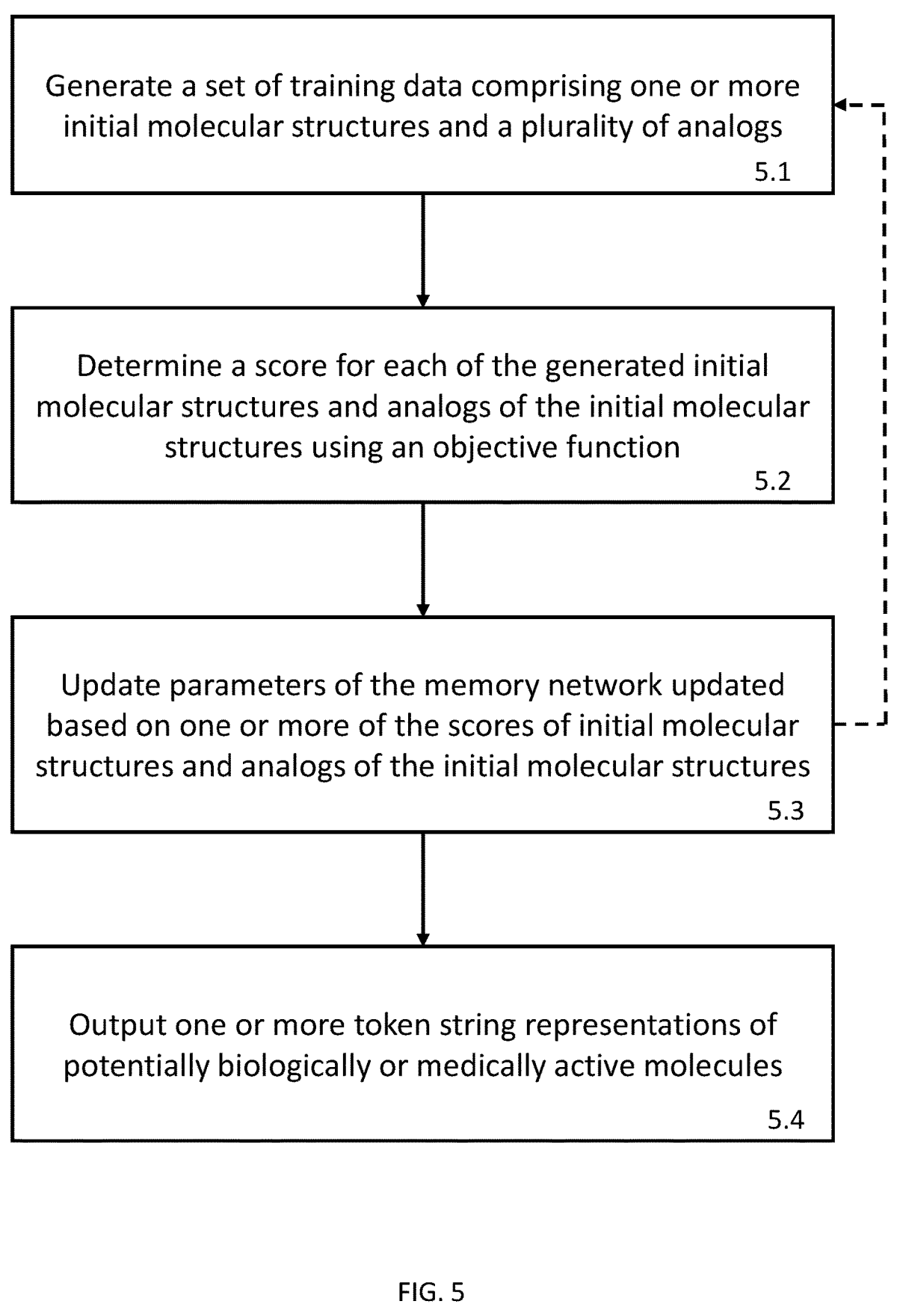

Generate a set of training data comprising one or more initial molecular structures and a plurality of analogs 5.1

Determine a score for each of the generated initial molecular structures and analogs of the initial molecular structures using an objective function 5.2

Update parameters of the memory network updated based on one or more of the scores of initial molecular structures and analogs of the initial molecular structures 5.3

Output one or more token string representations of potentially biologically or medically active molecules 5.4

FIG. 5

MOLECULAR DESIGN USING LOCAL EXPLORATION

CROSS-REFERENCE TO RELATED APPLICATIONS

The present application is the national stage entry of International Patent Application No. PCT/EP2022/051953, filed on Jan. 27, 2022, and claims priority to EP 21315009.7, filed on Jan. 27, 2021, the disclosures of which are incorporated herein by reference.

TECHNICAL FIELD

This specification relates to systems and methods for generating potential medicinal molecules using memory networks.

BACKGROUND

Finding new drugs is a long, costly and difficult problem, with potential failure all along the drug discovery pipeline and an overall success rate close to only 4%. Lead-optimization, where medicinal chemists refine bioactive molecules into potential drugs, takes a major part of the time and cost in the discovery pipeline. Finding a good drug candidate requires finding a molecule that is active on the target of interest while satisfying multiple criteria, such as those related to safety and ADME (Absorption, Distribution, Metabolism, Excretion). In this respect, lead-optimization can be viewed as a multi-objective optimization problem in chemical space.

There has been a recent surge of interest in generative models for de-novo drug design and their application in the drug discovery pipeline. Generative models have been studied for two types of tasks: distribution learning and goal-oriented learning. Distribution learning aims at reproducing the distribution of a known dataset, in order to sample a large library of molecules similar to the initial dataset used to train the generative model. Goal-oriented learning, on the other hand, takes as input a scoring function and aims at finding the molecules with the highest scores. Applying generative models to lead optimization can actually be understood as a special case of goal-oriented learning, where the scoring function reflects the adequacy of the molecule to the different project objectives. Distribution learning benchmarks are also frequently used to assess whether a model has learnt to generate drug-like molecules, and will be a good starting point for goal-oriented learning.

SUMMARY

According to a first aspect of this specification, there is described a computer implemented method of generating analogs of a molecule. The method comprises: receiving one or more initial molecular structures; generating one or more of token string representations for each of the one or more initial molecular structures, each token string representation corresponding to an analog of a corresponding initial molecular structure. Generating the token string representations of analogs comprises, for each further token string representation: sequentially processing a token string representation of a substructure of the corresponding initial molecular structure using a memory network; and subsequent to processing the token string representation of a substructure, sampling one or more additional tokens using the memory network. The token string representations each comprise a plurality of tokens representing predefined structures of a molecule. The memory network encodes a sequential probability distribution on the tokens using an internal state of the memory network.

Sequentially processing a token string representation of a substructure of the corresponding initial molecular structure may comprise: selecting a starting position in the corresponding initial molecular structure; traversing the corresponding initial molecular structure from the starting position using a traversal rule to generate a token string representation of the corresponding initial molecular structure; and generating the token string representation of a substructure of the corresponding initial molecular structure by taking a sequence of tokens from the token string representation of the corresponding initial molecular structure, wherein the sequence of tokens begins at a first token corresponding to the starting position.

Sequentially processing a token string representation of a substructure of the corresponding initial molecular structure may comprise: selecting a starting position in the corresponding initial molecular structure; traversing the corresponding initial molecular structure from the starting position for a plurality of steps using a traversal rule to generate a sequence of tokens corresponding to the token string representations of a substructure of the corresponding initial molecular structure.

The length of the sequence of tokens may be selected from a pre-defined distribution over substructure sizes. The traversal rule may be selected from a plurality of valid traversal rules using a selection rule. The starting position may be a randomly selected atom or structure in the first molecular structure.

Sequentially processing a token string representation of a substructure of the corresponding initial molecular structure may comprise sequentially reading the token string representation of the substructure into the memory network. The internal state of the memory network may be updated after each token of the token string representation of the substructure is read in. Sampling one or more additional tokens using the memory network may comprise updating the internal state of the memory network after each additional token is sampled.

One or more further tokens may be sampled until an end of string token is sampled and/or a string size limit is reached.

Receiving one or more initial molecular structures may comprise generating one or more token string representations of initial molecular structures using a memory network.

According to a further aspect of this specification, there is described a computer implemented method of generating potentially biologically or medically active molecules. The method comprises: generating one or more initial molecular structures and a plurality of analogs of the initial molecular structures using any of the analog generation methods described herein; determining a score for each of the generated initial molecular structures and analogs of the initial molecular structures using an objective function; updating parameters of the memory network based on one or more of the scores of initial molecular structures and analogs of the initial molecular structures; and outputting one or more token string representations of potentially biologically or medically active molecules based on the memory network with updated parameters.

Updating parameters of the memory network based on one or more of the values of the objective functions for the further molecular structures may comprise: generating an ordered list of molecular structures by ordering the initial molecular structures and analogs of the initial molecular structures based on the determined scores; and updating parameters of the memory network based on a predefined number of highest-scoring molecular structures in the ordered list of molecular structures.

The token string representations may be SMILES representations. Alternatively, the token string representations may be 1-letter and/or 3-letter amino acid representations.

According to a further aspect of this specification, there is described a method of synthesising a potential biologically or medically active molecule. The method comprises: generating a structure of a potential biologically or medically active molecule using any of the methods described herein; and synthesising the potential biologically or medically active molecule based on the generated structure.

According to a further aspect of this specification, there is described a biologically or medically active molecule generated or synthesised based on any of the methods described herein.

According to a further aspect of this specification, there is described a drug comprising at least one biologically or medically active molecule synthesized based on any of the methods described herein.

According to a further aspect of this specification, there is described a system comprising one or more processors and a memory, the memory comprising computer readable instructions that, when executed by the one or more processors, causes the system to perform any one or more of the computer implemented methods described herein.

According to a further aspect of this specification, there is described a computer program product comprising computer readable code that, when executed by a computing system, causes the computing system to perform any one or more of the methods described herein.

BRIEF DESCRIPTION OF THE FIGURES

Embodiments will now be described by way of non-limiting examples with reference to the accompanying drawings, in which:

FIG. 4 shows a flowchart of an example method of generating analogs of a molecule;

FIG. 5 shows a flowchart of an example method of generating potentially biologically or medically active molecules;

DETAILED DESCRIPTION

In-silico molecular optimization, whose goal is to design molecule optimized with respect to multiple computable properties, has stirred major interest in recent years due to its potential applications in drug discovery. Language models trained on a large corpus of drug-like molecules, coupled with reinforcement learning, have been shown to produce high quality (in terms of drug-likeness) molecules, yet still slightly lag behind other optimization methods with respect to the scores attained.

Language models with reinforcement learning, while being able to perform global search within chemical space, often fail to perform local search, i.e. fine-grained modifications to molecules. This specification describes systems and methods that allow a language model to explore locally around a given molecule. Including the possibility of fine-grained modifications by the language model within the reinforcement learning process allows the method to reach state-of-the-art results on a comprehensive set of molecular optimization benchmarks. As used herein the term "local search" is preferably used to connote fine grained edits to molecules say close to previously identified molecules. The tem "explore locally" is preferably used to connote exploring structural analogs of an initial model, guided by a given probability distribution in chemical space. Such a probability distribution may quantify a drug-likeness of a molecule (see, for example, Segeler et al. "Generating Focused Molecule Libraries for Drug Discovery with Recurrent Neural Networks" ACS Cent. Sci. 2018, 4, 1, 120-131). These can be contrasted to a global search, which searches over all possible/a much larger space of potential molecular structures.

Figure 1:
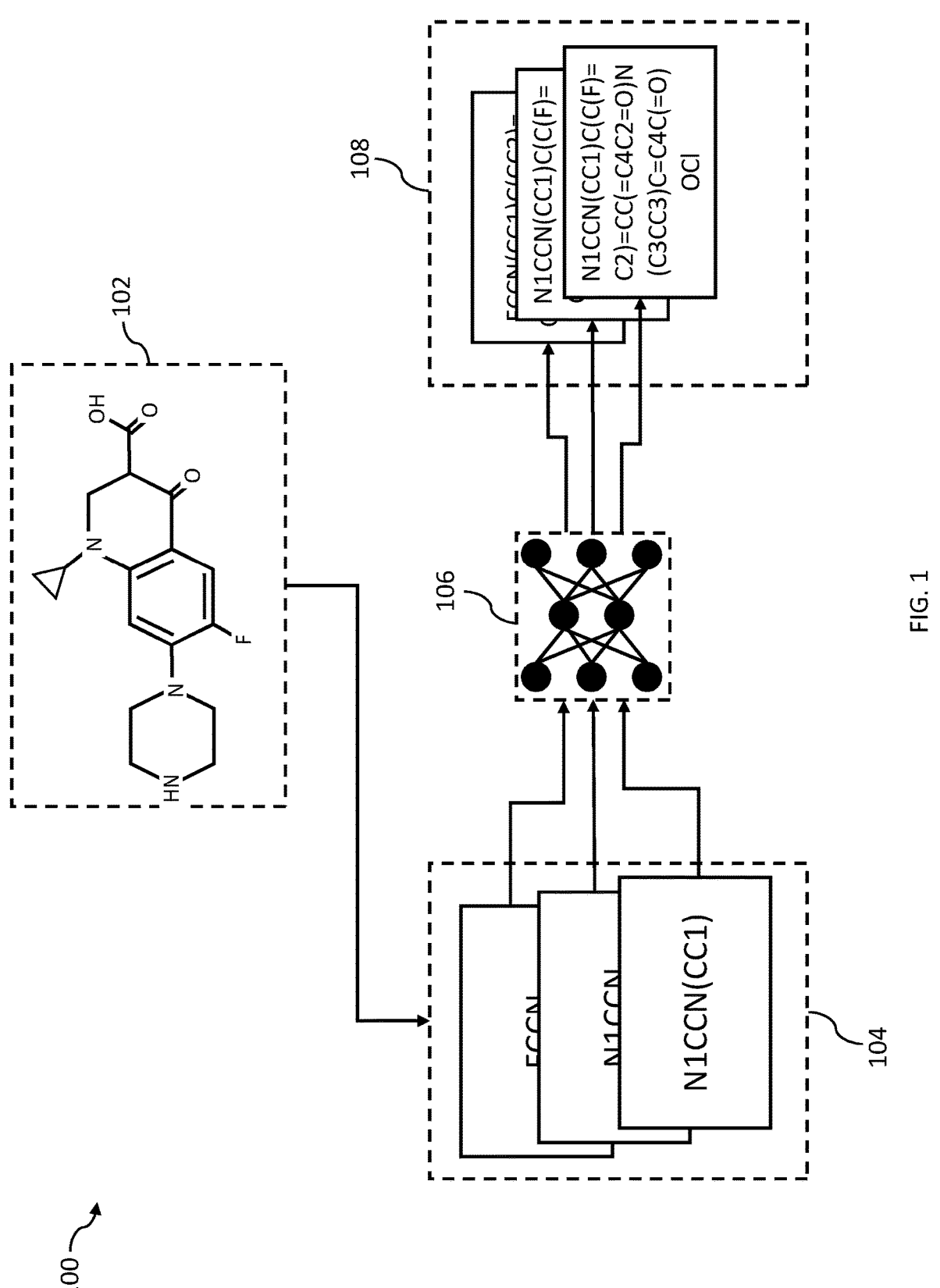
FIG. 1 shows a schematic overview of an example method of generating molecular analogs of an initial molecule.

FIG. 1 shows a schematic overview of an example method 100 of generating molecular analogs of an initial molecule. The method explores locally around an initial molecular structure in order to generate analogs of the initial molecule.

One or more initial molecular structures 102 are received, in the example shown represented by a molecular graph. In some embodiments, each of the one or more initial molecular structure is generated using a memory network 106 that generates token string representations corresponding to the initial molecular structure 102 (herein also referred to as the "first molecular structure" and/or the "original molecular structure"), for example as described below in relation to Process 1. Token string representations of substructures 104 of the initial molecular structure 102 are processed by the memory network 106 to generate one or more (e.g. a plurality) of token string representations of analogs 108 the initial molecular structure 102. Analogs 108 of the initial molecular structure 102 may also be referred to herein as "further molecular structures".

Generating a token string representation of a further molecular structures 108 comprises sequentially reading a token string representation of a substructure of the initial molecular structure 102 into the memory network 106, and then sampling additional tokens for the token string using the memory network 106. Thus, each token string representing an analog 18 comprises a first part, comprising the token string of the substructure 104, and a second part comprising the sampled tokens. In effect, the memory network 106 is used to explore local analogs 108 to the initial molecular structure 102.

A token string representing a molecular structure comprises string of tokens (also referred to as "characters"). Each token may correspond to an atom, structure or denote other structural information, such as opening or closing of cycles (e.g. by use of numbers) and branches (e.g. by use of parentheses), stereochemistry or multiple bonds (e.g. by use of the symbol "=" for a double bond, etc.). The tokens may, for example, include the atomic symbols of atoms. The tokens may further comprise tokens representing the opening and closing of branches of the molecule, e.g. opening and closing parenthesis to represent the start and end of a branch respectively. The tokens may comprise tokens representing molecular building blocks, such as amino acids, peptides or other multi-atom structures. The set of possible tokens is referred to as the token "alphabet".

In some embodiments, the token string comprises an "initialisation" token (e.g. "GO") that indicates the start of the token string 102. The token string may further comprise an "end-of-string" token indicating the end of the token string 102 (e.g. "EOS").

An example of such a character string representation is the SMILES language (see, for example, "*SMILES—A Language for Molecules and Reactions*", Weininger D., Handbook of Chemoinformatics 2008, 80-102). To generate a SMILES representation of a molecule from a molecular graph, cycles are broken down and marked with numbers, and a starting atom is chosen. A SMILES string is obtained by printing the symbol of the nodes encountered in a depth-first traversal starting at the chosen atom, with parentheses indicating branching points in the graph. For a given molecular graph, there are at least as many SMILES as possible starting atoms. For example, there may be as many SMILES as the number of starting atoms multiplied the number of valid traversal rules for the molecular graph. A corresponding molecular graph can be easily retrieved from a given SMILES.

A further example of such a token string representation may comprise a one-letter and/or three-letter amino acid representation. Other examples of token string representations will be familiar to those skilled in the art.

The memory network 106 is a machine-learned model that can generate tokens based on an internal state, h, of the memory network 106 (also referred to herein as a "hidden state"). Initial tokens may be input/read into the memory network 106 to constrain the initial tokens of the output token string, though the memory network 106 can also be configured to generate an output string with no network input, or with only an "initialisation" token input. The memory network may have been trained example using the method described in relation to FIG. 6.

The internal state of the memory network 106 is updated after a token is either read into the memory network 106 or generated/sampled by the memory network 106. The internal state is updated based on learned parameters of the memory network, $\theta$. The internal state of the memory network 102 stores information about the tokens processed so far by the network 102.

The memory network 106 can generate an output token string representing a molecule in a sequential fashion by modelling a conditional probability distribution over characters/tokens of the string, conditioned on the characters in the string so far. The memory network 106 relies on its internal state h to process information about the previous tokens, $\{x_0, \ldots, x_{t-1}\}$ in the token string and generate the next output token $x_t$. The memory network 106 models the conditional probability $P(x_t|x_0, \ldots, x_{t-1})$ as $P(x_t|h_{t-1})$, i.e. the conditional probability is encoded using the hidden state.

The memory network 106 may be a memory neural network. An example of such a network is a Recurrent Neural Network (RNN), such as a Long-Short-Term Memory (LSTM) network. In such embodiments, reading a token string representation into the memory network may comprise sequentially inputting the token string into the memory network 106.

When used to generate an initial molecular structure 102, the memory network 106 may not have any tokens read into it (or equivalently, only have an initialisation token read into it). The memory network 106 thus samples tokens from scratch to generate the token string representation corresponding to an initial molecular structure 102. The process may, in some embodiments, be represented by the following process:

---

Process 1: Generating a first molecular token string

| Result: | Molecular token string |
|---|---|
| initialise | $h_0$ ; |
| | $x_0$= GO ; |
| | t= 1 ; |
| while $x_t \neq$ EOS do | |
| | sample $x_t$ from $P(x_t \mid h_{t-1})$ and update $h_{t-1}$ to $h_t$ ; |
| | t=t+1 ; |
| end | |
| Output: $x_0, ..., x_t$ | |

---

Here, GO and EOS are the initial and final tokens of the string respectively, and $x_i$ is the token at position i in the token string.

When generating a token string representation of an analog 108 from a token string representation of a substructure 104 of an initial molecular structure 102, part of the molecular graph of the first molecular structure 102 is fixed and sampling is performed to determine the remaining part of the molecule. Examples of methods of determining token string representations of substructures 104 from an initial molecular structure 102 are described in relation to FIG. 2.

In some embodiments, generating a token string representation of an analog 108 comprises sequentially reading the tokens of the token string representation of a substructure 104 into the memory network 106, and updating the internal state, h, of the memory network after reading in each token. Once the tokens of the substructure 104 have been read into the memory network 106, additional tokens are sampled and added to the token string, updating the internal state of the memory network 102 after each token is added. The update to the internal state is based on the value of the sampled token. Tokens are sampled until an end-of-string token is sampled, or a predetermined number of tokens have been sampled.

The resulting token string provides a token string representation of an analog 108 to the initial molecular structure 102.

In some embodiments, given a token string representation, s, of an initial molecular structure 102, the process of generating analogs may be represented by the following process:

---

Process 2: Exploring a token string from a given step

| Data: | Token string of first molecule $s=s_0, ..., s_t$ , |
|---|---|
| | Probability distribution $P(x_t \mid x_0, ..., x_{t-1})$ , |
| | step |
| $x \leftarrow \{ \}$; | |
| for t $\leftarrow$ 0 to step do | |
| | $x_t \leftarrow s_t$ ; |
| | t $\leftarrow$ t+1; |
| end | |
| while EOS not reached do | |
| | $x_t \sim P(x_t \mid x_0, ..., x_{t-1})$; |
| | t $\leftarrow$ t+1; |
| end | |
| Output: $\{x_0, ..., x_t\}$ | |

---

Here, $P(x_t|x_0, \ldots, x_{t-1})$ is the conditional probability distribution over tokens, for example as encoded by the memory network 106, "~" indicates sampling, and step is the number of tokens to be taken from s before sampling starts, i.e. the size of the substructure being explored. s may be the token string representation of the initial molecule 102 output by the memory network that generated it, or may be an alternative token string representation of the initial molecule 102, for example generated as described in relation to FIG. 2A.

Molecular structures corresponding to the output token string representations of analogs 108 of the initial molecule 102 may be used to augment a training dataset for performing a reinforcement learning process to generate optimised molecular structures. The use of these analogs as training data for a reinforcement learning process allows the reinforcement learning process to locally explore the space of potential molecules around a known molecule, which can result in the generation of improved/better optimised molecular structures for use in medicaments or other pharmaceutical products. Incorporation of these molecules into medicaments or other pharmaceutical products can result in improved treatments for medical conditions. An example of such a process is described below in relation to FIG. 3. Alternatively or additionally, molecules corresponding to the output token string representations of analogs 108 of the initial molecule 102 may be synthesized. The synthesized molecules may be tested to determine which of them are medicinally/biologically active. Molecules with desirable medical or biological properties may be incorporated into a pharmaceutical product, such as a drug or medicine.

Figure 2:
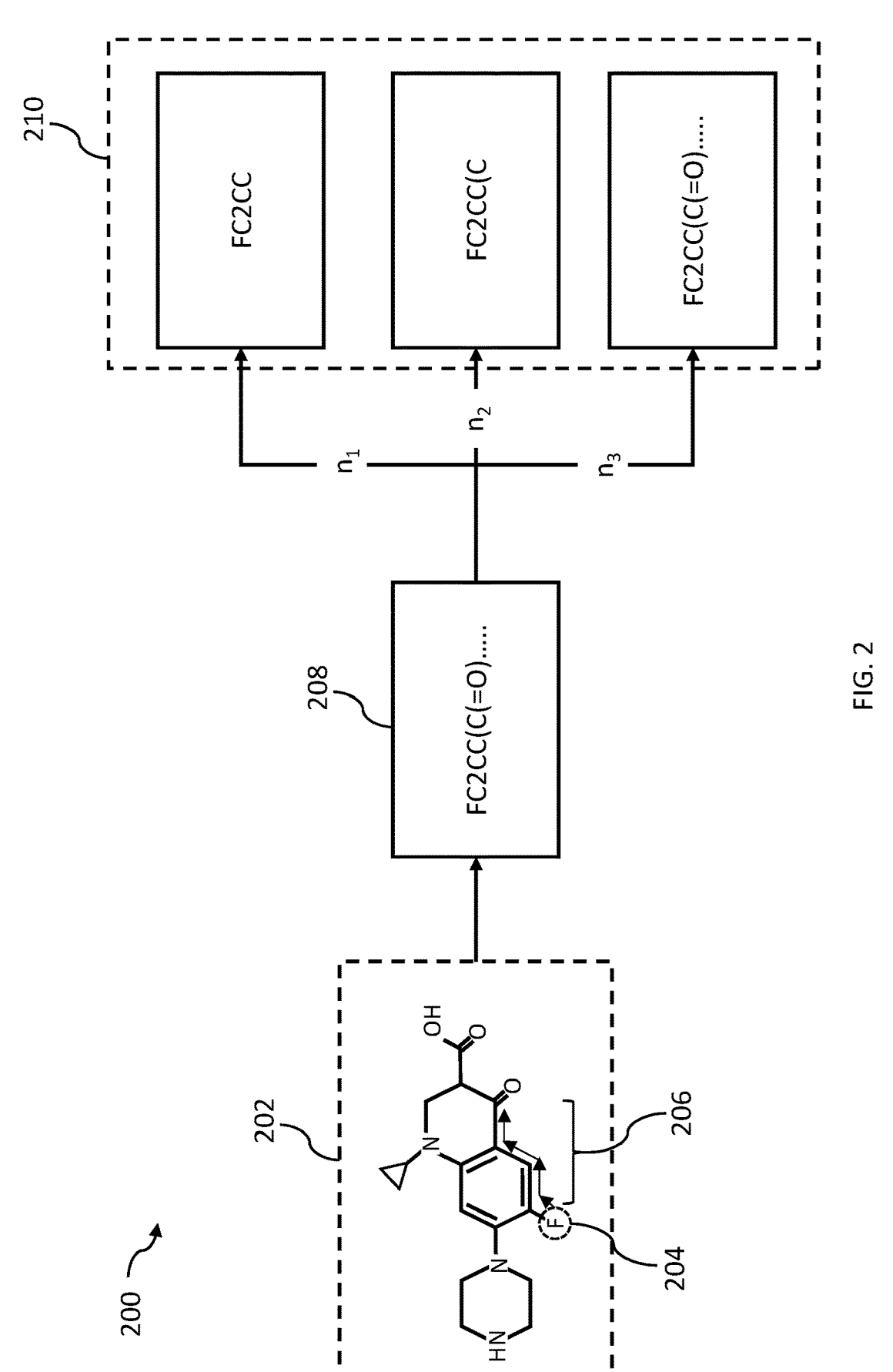
FIG. 2 shows a schematic overview of a method of generating substructures of a known molecular structure.

FIG. 2 shows a schematic overview of a method 200 of generating substructures of a known molecular structure.

For a given molecular structure 202, there may be a plurality of valid token string representations of that molecular structure 202. Different valid token strings may correspond to starting the token string from different atoms in the molecular structure 202. Alternatively or additionally, a different valid token strings may correspond to different valid traversal rules for the molecular structure 202. Thus, given a molecular structure 202, different token string representations of that molecular structure 202 may be generated using different starting atoms and traversal rules for the molecular graph. This property of the token string representations can be exploited to generate token string representations of different substructures of a molecule.

To generate token string representations of substructures of a molecule 210, a random atom 204 in the molecular structure 202 is selected as a starting point, and the molecular structure 202 traversed to generate the token string. A molecular graph 202 corresponding to the molecule may be traversed from the random atom according to a traversal rule 206. The traversal rule may be a fixed traversal rule (e.g. a canonical traversal rule) or selected randomly from a set of traversal rules that generate valid token string representations (a "valid traversal rule"). A token string representation 208 of the molecule that starts from the random atom 204 may generated as the molecular structure is traversed. Such token string representations 208 of the molecule that correspond to different starting atoms 204 and/or different traversal rules 206 may be referred to as "alternative token string representations" of the molecular structure 202. The process of generating such a token string 208 from a known molecular structure, m, may be referred to as "RandomiseTokenString(m)".

Once a token string representation 208 of the molecule has been generated, token strings corresponding to substructures 210 of that molecule may be generated by takin the first n of the tokens in the token string, where n is an integer number. A plurality of token string representations of substructures 210 of the molecule may be generated by varying the value on n, for example by incrementing it from an initial value, or randomly sampling from a distribution, $Q_n$, over the size of n. Many examples of such a distribution are possible. For example, the distribution may be proportional to n raised to some power greater than one, e.g. $n^3$, thus favouring larger substructures.

The token string representations of substructures of a molecule 210 can be used to explore analogs to the original molecule as described in relation to FIG. 1. An example of a process that may be used to generate analogs to a given molecule, m, maybe given by:

---

Process 3: Generating token analogs of a molecular structure

Data:      molecular structure m, $Q_n$, $n_{samples}$
Result:      Token string representations of analogs of m
analogs ← { };
for atom A in m do
  |   s ← Randomise TokenString(m);
  |   for i ← 0 to $n_{samples}$ do
  |  |    step ~ $Q_n$
  |  |    analogs ← analogs ∪ {ExploreFromStep(s, step)}
  |   end
end
Output: analogs

---

The output of this process is a set of token string representations of analogs of the molecule m, i.e. molecules that share substructures with m.

In some embodiments, alternative methods of generating substructures of a known molecule can be used. For example, a token string representation of a substructure may be generated by selected a starting atom, e.g. at random, and traversing the molecular graph of the molecule using a traversal rule for an integer number of steps $n_{steps}$. A plurality of token string representations of substructures 210 of the molecule may be generated by varying the value on $n_{steps}$ (for example by incrementing it from an initial value, or randomly sampling from a distribution, $Q_n$, over the size of $n_{steps}$), varying the traversal rule (for example by selecting it from a set of valid traversal rules) and/or using different starting atoms (e.g. selecting other starting atoms at random).

Figure 3:
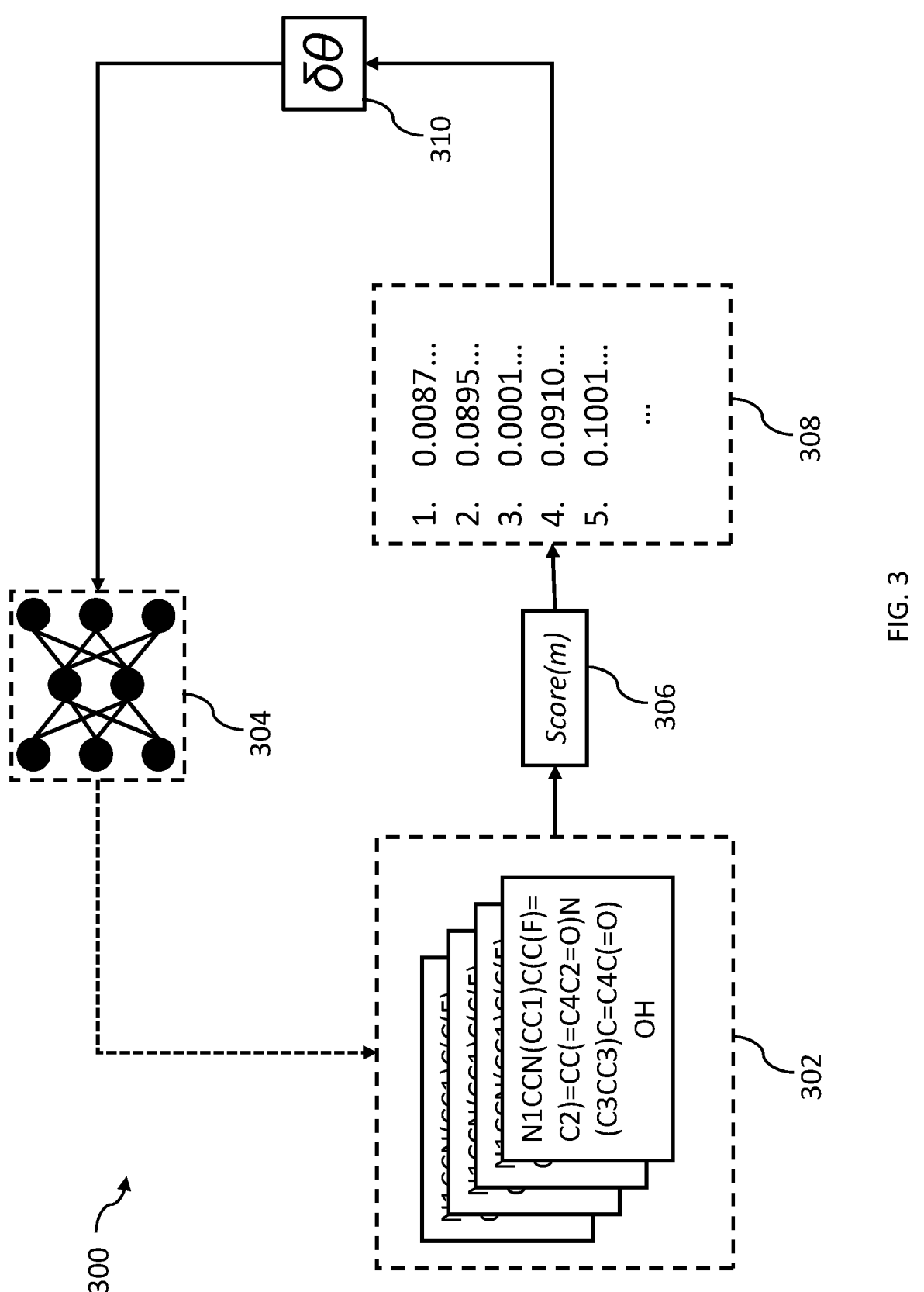
FIG. 3 shows an example of a method for optimising potential biologically or medically active molecules using reinforcement learning.

FIG. 3 shows an example of a method 300 for optimising potential biologically or medically active molecules using reinforcement learning. Use of the method can result in the discovery improved and/or better optimised biologically and/or medicinally active molecules. These molecules can be synthesised and incorporated into pharmaceutical products, resulting in more effective treatments for medical conditions.

A training dataset 302 comprising one or more initial molecular structures and a plurality of analogs of one or more of the initial molecular structures is used to fine tune parameters of a memory network 304. The memory network 304 is the same memory network 304 used to generate the analogs from the initial molecular structures (i.e. memory network 106 of FIG. 1). The goal of fine tuning the memory network 304 is to train the memory network 304 to generate token string representations of molecules that optimise an objective function 306.

Each of the molecular structures in the set of training data 302 is scored using an objective function 306, Score(m). Based on one or more of the scores 308, parameter updates 310 for the memory network 304 may be determined and applied to the memory network 304. For example, an optimisation routine, such as stochastic gradient ascent or the like, may be applied to the objective function 306 in order to determine updates 310, 6e, to the parameters of the memory network 304.

The objective function 306 provides a score indicative of how likely the generated structure is to have one or more biological or medicinal properties. Examples of such objective functions include, but are not limited to: log P; Quantitative Estimate of Drug Likeness (QED); QSAR/QSPR models; scores provided by molecular docking or other physics-based methods; and/or one or more of the benchmarks provided in the Guacamol suite.

In some embodiments, the set of training data 302 comprises a plurality, $n_{train}$, of molecular structures selected from initial molecular structures and analogs of the one or more of the initial molecular structures using a filtering process. A plurality, $n_{train}$, of initial molecular structures may be generated using the memory network 304. A score for each of these is determined using the objective function 306. A predetermined number, $k \leq n_{train}$, of the initial molecules are selected based on their score. For example, the top k best scoring molecular structures may be selected. The selected initial molecules each have a plurality, $n_{explore}$, of analogs generated, for example using the method described in relation to FIG. 1. A score for each of these analogs is determined using the objective function 306. The set of training data is generated by taking a plurality, $n_{train}$, of the top scoring initial molecular structures and analogs. In other words, the set of generated analogs is combined with the set of initial molecular structures, and the top $n_{train}$ scoring molecular structures are selected to be part of the set of training data 302.

Once updated, the memory network 304 may be used to generate a new set of training data using the method described in relation to FIG. 1. The molecular structures in this new training dataset are scored using the objective function, and one or more of the scores are used to determine further updates to the parameters of the memory network 304. This process may be iterated until a threshold condition is satisfied. For example, the threshold condition may be a threshold number of iterations, $n_{step}$, being reached.

An example of a method for optimising potential biologically or medically active molecules using reinforcement learning may be provided by the following process:

---

Process 4: Reinforcement learning with local exploration

---

Data:    $n_{steps}$, $n_{explore}$, $n_{samples}$, $n_{train}$, k, $Q_n$, score(m), $P_0$
Result:    Optimised molecules with respect to score
for t←0 to $n_{steps}$ do
  |    strings ← SampleStrings($P_t$, $n_{samples}$);
  |    training ← { } ;
  |    reorder strings by ascending values of score ;
  |    for i ← 0 to $n_{train}$ do
  |    |    s ← i-th element of strings;
  |    |    if i <= k then
  |    |    |    training ← training ∪ {ExploreStrings(s, $Q_n$, $n_{explore}$)} ;
  |    |    end
  |    |    else
  |    |    |    training ← training ∪ {s}
  |    |    end
  |    end
  |    re-order training by ascending values of score ;
  |    keep only top $n_{train}$ token strings in training;
  |      $P_{t+1}$ ← TrainPolicyOnBatch($P_t$, training)
end

---

Here, $n_{steps}$ is the threshold number of iterations for the method, $n_{samples}$ is the number of initial molecular structures generated at each iteration, $n_{explore}$ is the number of analogs generated for each of the k molecules selected for local exploration, $n_{train}$ is the size of the set of training data at each iteration, $Q_n$ is a distribution over substructure sizes, "score (m)" is the objective function for molecule m, and $P_0$ is the initial conditional probability distribution encoded by the memory network 304 (i.e. encoded by the parameters of the memory network 304). The sets "strings" is a list of token string representations of molecules and the set "training" is the set of training data for the current iteration. The function "SampleStrings($P_t$, $n_{samples}$)" generates $n_{samples}$ token string representations of initial molecular structures, for example using the method shown in Process 1. The function "ExploreStrings(s, $Q_n$, $n_{explore}$)" generates $n_{explore}$ analogs of the token string molecular structure s based on $Q_n$, for example using the method described in relation to FIG. 1. The function "TrainPolicyOnBatch($P_t$, training)" updates the conditional probability distribution encoded by the memory network 304 based on the training data (i.e. determines updates to the parameters of the memory network 304 based on the training data, as described in relation to FIG. 3).

The method of FIG. 3 may be used to generate potential biologically or medicinally active molecules. For example, once fine-tuned, the memory network can be used to generate token string representations of molecules. Due to the fine-tuning process, these will have a higher likelihood of corresponding to a molecule that scores highly with respect to the objective function.

Alternatively or additionally, potential biologically or medicinally active molecules may be generated during the fine-tuning/optimisation process itself. During each iteration of the parameter update process, the top scoring molecules out of the set of training data for the current iteration and the training data from the previous iterations may be stored. These are then output at the end of the method as potential biologically or medicinally active molecules For example, at each iteration a list of molecules may be generated by ordering the union of the molecules in the current set of training data and the molecules stored from the previous sets of training data (i.e. from previous iterations). A predetermined number, $n_{store}$, of the top scoring molecules may then be stored. In other words, the top $n_{store}$ molecules out of all the molecules generated so far in the method are kept at each iteration.

The potential biologically or medicinally active molecules output at the end of the fine-tuning/optimisation process may be synthesised to determine if they are indeed biologically or medically active. If so, thy may be incorporated into a medicinal/pharmaceutical product, such as a drug, which can result in improved treatments for medical conditions.

FIG. 4 shows a flowchart of an example method of generating analogs of a molecule, such as a potential biologically or medically active molecule. The method may be performed by a computing system, such as the system described below in relation to FIG. 7. The method may correspond to the methods described in relation to FIGS. 1 and 2.

At operation 4.1, one or more initial molecular structures are received. The one or more initial molecular structures may have been generated using token string representations of initial molecular structures generated using a memory network, for example as described in relation to FIG. 1 and/or Process 1.

At operation 4.2, one or more of token string representations of analogs of initial molecular structures are generated. Each token string representation represents to an analog of a corresponding initial molecular structure.

Generating the one or more of token string representations of analogs of initial molecular structures comprises, for each further token string representation: sequentially processing a token string representation of a substructure of the corresponding initial molecular structure using a memory network; and subsequent to processing the token string representation of a substructure, sampling one or more additional tokens using the memory network.

Sequentially processing a token string representation of a substructure of the corresponding initial molecular structure may comprise sequentially reading the token string representation of the substructure into the memory network, i.e. inputting the token string into the memory network, starting from the initial token. The internal state of the memory network is updated after each token of the token string representation of the substructure is read in, based on the parameters of the memory network.

Sampling one or more additional tokens using the memory network comprises selecting a token to add to the token string based on the current internal state of the memory network. Once a token is selected and added to the token string, the internal state of the memory network is updated based on the parameters of the memory network. Tokens are sampled until an end-of-string token is reached, a predetermined number of tokens has been sampled and/or a predetermined token string length is reached.

The token string representations of substructures of an initial molecule may be generated by selecting a starting position in the initial molecular structure and traversing said molecular structure using a traversal rule to generate an alternative token string representation of the initial molecule, then taking the first n tokens of the alternative token string representation.

Alternatively, the token string representations of substructures of an initial molecule may be generated by selecting a starting position in the initial molecular structure and traversing said molecular structure using a traversal rule for n steps to generate an alternative token string representation of the initial molecule.

Irrespective of which of these methods is used, the number of tokens taken to form the substructure, n, may be selected from a distribution $Q_n$. The starting position in the initial molecular structure may correspond to a randomly selected atom. The traversal rule may, for example, be a canonical traversal rule, or may be selected from a list of valid traversal rules.

FIG. 5 shows a flowchart of an example method of generating potentially biologically or medically active molecules. The method may be performed by a computing system, such as the system described in relation to FIG. 7. The method may correspond to the methods described in relation to FIG. 3, such as Process 4.

At operation 5.1, a set of training data comprising one or more initial molecular structures and a plurality of analogs of the initial molecular structures is generated, for example using any of the methods described in relation to FIGS. 1-3. These will be used as a set of training data for fine tuning the memory network.

At operation 5.2, a score is determined for each of the generated initial molecular structures and analogs of the initial molecular structures using an objective function. The objective function provides a score indicative of how likely the generated structure is to have one or more biological or medicinal properties. Desirable medicinal and/or biological properties may positively contribute to the objective function. Undesirable medicinal and/or biological properties may negatively contribute to the objective function.

At operation 5.3, parameters of the memory network are updated based on one or more of the scores of initial molecular structures and analogs of the initial molecular structures.

In some embodiments, the scores of a plurality of the best scoring molecular structures in the set of training data are used to generate the updates, with the remaining molecular structures not being used. An optimisation routine may be applied to the objective function for the best scoring molecules to determine the updates. For example, a gradient-based optimisation routine, such as gradient ascent, may be applied to determine the parameter updates. Many other examples of optimisation routines that could be used will be apparent to those skilled in the art.

Operations 5.1 to 5.3 may be iterated until a threshold condition is satisfied. The threshold condition may be a threshold number of iterations. At each iteration, the highest scoring molecules out of the current set of training data and previous sets of training data may be stored for output once the threshold condition is satisfied.

At operation 5.4, one or more token string representations of potentially biologically or medically active molecules are output. The one or more token string representations of potentially biologically or medically active molecules may be generated using the memory network with updated parameters.

Alternatively or additionally, the highest scoring molecules stored during the training iterations may be output. In some embodiments, a final set of initial molecules may be generated after the final iteration, and the list of top scoring molecules updated based on the scores of these final initial molecules.

In either case, the output one or more token string representations of potentially biologically or medically active molecules may be said to be based on memory network with updated parameters.

Figure 6:
FIG. 6 shows a schematic overview of an example method of training a memory network to generate a molecular structure.

FIG. 6 shows a schematic overview of an example method 600 of training a memory network to generate a molecular structure. The method may be performed by a computing system, such as the system described in relation to FIG. 7. The method is a method of training a memory network to generate token string representations of molecules, and may be used prior to the methods described in relation to FIGS. 1-5 to initially train the memory network.

During training, the memory network 604 receives an initial input 602 and generates a token string representing a molecule 606. An objective function 608 (also referred to herein as a "loss function") is used to determine parameter updates to the memory network 606 based on the output token string 606. The input 602 may, for example, be a start-of-string token. The input 602 may alternatively be a token string representing a known start to a molecule in the training dataset.

The memory network 604 generates output token strings 606 in a sequential fashion by modelling the conditional probability distribution over tokens, conditioned on the beginning of a token string, i.e. the token string so far in the memory network 604. Let $s=x_0, \ldots, x_n$ the tokenized version of a molecular string, with $\{x_i\}$ being tokens/characters from a language, such as SMILES. In some embodiments, $x_0$ and x, denote respectively start-of-string and end-of-string tokens. The memory network 604 models $P(x_t|x_0, \ldots, x_{t-1})$, i.e. the conditional probability of a token given the previous tokens in the string.

The memory network 604 is trained on a training dataset of drug-like molecules to predict a next token given the beginning of the sequence. The molecules in the training dataset may be taken from a database of drug-like molecules. An example of such a database is ChEMBL, though it will be appreciated that other databases may alternatively be used. The drug-like molecules are represented as a token string in the database or converted to one before input into the memory network 602. A validation dataset, used to validate the memory network 604, may also be generated from a database of drug-like molecules. This database may be a subset of the database of drug-like molecules.

The training dataset may be a generic dataset, comprising diverse drug-like compounds. A memory network 604 trained on such a dataset may be able to explore a large and varied chemical space when generating potentially interesting molecules. Alternatively, the training dataset may be a focussed training dataset, comprising molecules from one or more predefined chemical series (e.g. a single chemical series). A memory network 604 trained on such a dataset may be able to generate close analogues to a given chemical series. As an example, the training dataset may be generated from the database by extracting a predefined number (e.g. 1.2 million) of molecules from the database (e.g. ChEMBL) and filtering them using one or more predefined criteria. The predefined criteria may comprise one or more of: size; atoms present; and/or presence/absence of macrocycles.

Training is achieved by iteratively applying an optimisation procedure to a loss function 608, L, in order to determine updates to parameters of the memory network 604, e. The objective of the optimisation procedure may be to minimize the loss function 608 with respect to the memory network 604 parameters. The optimisation procedure may, for example, be a gradient descent method, such as stochastic gradient descent. The loss function may be a negative log-likelihood of the training set token strings, for example:

$$L(\theta) = -\sum_{t=1}^{T} \log P(x_t \mid x_0, \ldots, x_{t-1})$$

where $x_0$ is the initial token of the token string, and the token string has a total length of T tokens. The memory network 604 uses its current internal state, h, to process the information from the previous tokens, and models the conditional probability $P(x \mid x_0, \ldots, x_{t-1})$ as $P(x \mid h_{t-1})$. The internal state of the memory network 604 at step t, $h_t$, is dependent on the tokens in the string so far, $x_0, \ldots, x_t$, and the parameters of the memory network, e.

In some embodiments, the training dataset is augmented by enriching the training dataset with non-canonical token strings. This can improve the performance of the memory network 604 once trained.

Figure 7:
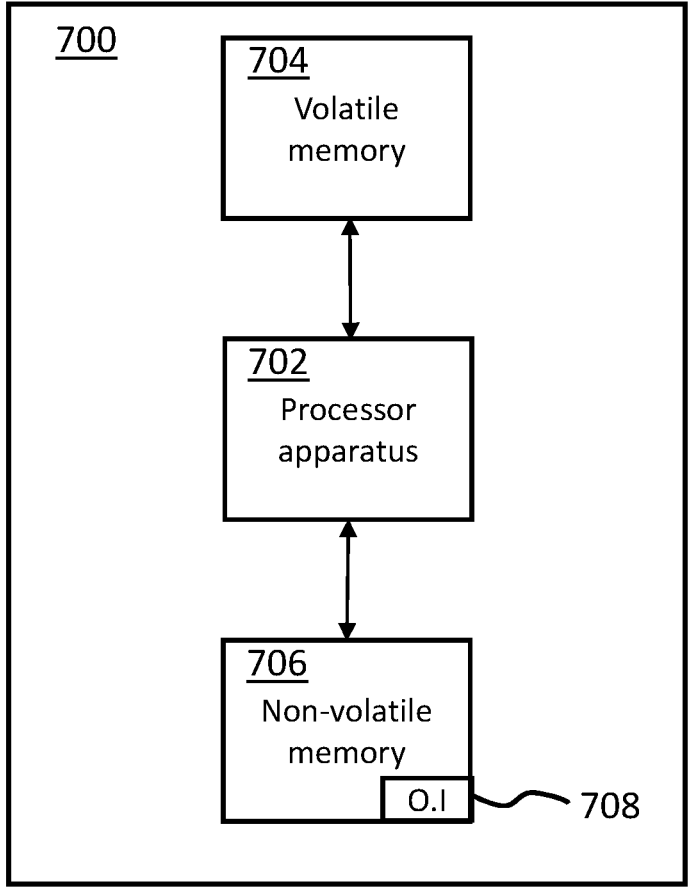
FIG. 7 shows a schematic example of a system/apparatus for performing any of the methods described herein.

FIG. 7 shows a schematic example of a system/apparatus 700 for performing any of the methods described herein. The system/apparatus shown is an example of a computing device. It will be appreciated by the skilled person that other types of computing devices/systems may alternatively be used to implement the methods described herein, such as a distributed computing system.

The apparatus (or system) 700 comprises one or more processors 702. The one or more processors control operation of other components of the system/apparatus 700. The one or more processors 702 may, for example, comprise a general-purpose processor. The one or more processors 702 may be a single core device or a multiple core device. The one or more processors 702 may comprise a Central Processing Unit (CPU) or a graphical processing unit (GPU). Alternatively, the one or more processors 702 may comprise specialised processing hardware, for instance a RISC processor or programmable hardware with embedded firmware. Multiple processors may be included.

The system/apparatus comprises a working or volatile memory 704. The one or more processors may access the volatile memory 704 in order to process data and may control the storage of data in memory. The volatile memory 704 may comprise RAM of any type, for example, Static RAM (SRAM), Dynamic RAM (DRAM), or it may comprise Flash memory, such as an SD-Card.

The system/apparatus comprises a non-volatile memory 706. The non-volatile memory 706 stores a set of operation instructions 708 for controlling the operation of the processors 702 in the form of computer readable instructions. The non-volatile memory 706 may be a memory of any kind such as a Read Only Memory (ROM), a Flash memory or a magnetic drive memory.

The one or more processors 702 are configured to execute operating instructions 708 to cause the system/apparatus to perform any of the methods described herein. The operating instructions 708 may comprise code (i.e. drivers) relating to the hardware components of the system/apparatus 700, as well as code relating to the basic operation of the system/apparatus 700. Generally speaking, the one or more processors 702 execute one or more instructions of the operating instructions 708, which are stored permanently or semi-permanently in the non-volatile memory 706, using the volatile memory 704 to store temporarily data generated during execution of said operating instructions 708.

Implementations of the methods described herein may be realised as in digital electronic circuitry, integrated circuitry, specially designed ASICs (application specific integrated circuits), computer hardware, firmware, software, and/or combinations thereof. These may include computer program products (such as software stored on e.g. magnetic discs, optical disks, memory, Programmable Logic Devices) comprising computer readable instructions that, when executed by a computer, such as that described in relation to FIG. 5, cause the computer to perform one or more of the methods described herein.

Any system feature as described herein may also be provided as a method feature, and vice versa. As used herein, means plus function features may be expressed alternatively in terms of their corresponding structure. In particular, method aspects may be applied to system aspects, and vice versa.

Furthermore, any, some and/or all features in one aspect can be applied to any, some and/or all features in any other aspect, in any appropriate combination. It should also be appreciated that particular combinations of the various features described and defined in any aspects of the invention can be implemented and/or supplied and/or used independently.

Although several embodiments have been shown and described, it would be appreciated by those skilled in the art that changes may be made in these embodiments without departing from the principles of this disclosure, the scope of which is defined in the claims and their equivalents.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A computer implemented method of generating analogs of a molecule, the method comprising:

receiving one or more initial molecular structures;

generating one or more token string representations for each of the one or more initial molecular structures, each token string representation corresponding to an analog of a corresponding initial molecular structure, wherein generating the one or more token string representations for each initial molecular structure comprises:

sequentially processing a substructure token string representation of a substructure of the corresponding initial molecular structure using a memory network, comprising sequentially reading the substructure token string representation of the substructure into the memory network for updating an internal state of the memory network; and subsequent to processing the substructure token string representation of the substructure, sampling one or more additional tokens using the memory network, wherein each of the one or more token string representations comprises a plurality of tokens representing predefined structures of a molecule, wherein the memory network encodes a sequential probability distribution on the plurality of tokens using the internal state of the memory network, and wherein the one or more additional tokens are sampled based on the sequential probability distribution.

2. The method of claim 1, wherein sequentially processing the substructure token string representation of the substructure of the corresponding initial molecular structure comprises:

selecting a starting position in the corresponding initial molecular structure;

traversing the corresponding initial molecular structure from the starting position using a traversal rule to generate the token string representation of the corresponding initial molecular structure; and generating the substructure token string representation of a substructure of the corresponding initial molecular structure by taking a sequence of tokens from the token string representation of the corresponding initial molecular structure, wherein the sequence of tokens begins at a first token corresponding to the starting position.

3. The method of claim 1, wherein sequentially processing the substructure token string representation of a substructure of the corresponding initial molecular structure comprises:

selecting a starting position in the corresponding initial molecular structure;

traversing the corresponding initial molecular structure from the starting position for a plurality of steps using a traversal rule to generate a sequence of tokens corresponding to the substructure token string representations of a substructure of the corresponding initial molecular structure.

4. The method of claim 3, wherein a length of the sequence of tokens is selected from a pre-defined distribution over substructure sizes; wherein the traversal rule is selected from a plurality of valid traversal rules using a selection rule; and/or wherein the starting position is a randomly selected atom in the first molecular structure.

5. The method of claim 1, wherein the internal state of the memory network is updated after each token of the substructure token string representation of the substructure is read in; and wherein sampling one or more additional tokens using the memory network comprises updating the internal state of the memory network after each additional token is sampled.

6. The method of claim 5, wherein the one or more further tokens are sampled until an end of string token is sampled and/or a string size limit is reached.

7. The method of claim 1, wherein receiving one or more initial molecular structures comprises generating one or more token string representations of initial molecular structures using a memory network.

8. The method of claim 1, wherein the memory network is a memory neural network.

9. The method of claim 8, wherein the memory neural network is a recurrent neural network.

10. A computer implemented method of generating potentially biologically or medically active molecules, the method comprising:

generating a plurality of analogs of one or more initial molecular structures, comprising:

receiving the one or more initial molecular structures;

generating one or more token string representations for each of the one or more initial molecular structures, each token string representation corresponding to an analog of a corresponding initial molecular structure, wherein generating the one or more token string representations for each initial molecular structure comprises:

sequentially processing a substructure token string representation of a substructure of the corresponding initial molecular structure using a memory network, comprising sequentially reading the substructure token string representation of the substructure into the memory network for updating an internal state of the memory network; and subsequent to processing the substructure token string representation of the substructure, sampling one or more additional tokens using the memory network, wherein each of the one or more token string representations comprises a plurality of tokens representing predefined structures of a molecule, wherein the memory network encodes a sequential probability distribution on the plurality of tokens using the internal state of the memory network, and wherein the one or more additional tokens are sampled based on the sequential probability distribution;

determining a score for each of the generated initial molecular structures and analogs of the initial molecular structures using an objective function;

updating parameters of the memory network based on one or more of the scores of the initial molecular structures and the analogs of the initial molecular structures; and outputting one or more token string representations of potentially biologically or medically active molecules based on the memory network with the updated parameters.

11. The method of claim 10, wherein updating parameters of the memory network based on one or more of the scores of the initial molecular structures and the analogs of the initial molecular structures comprises:

generating an ordered list of molecular structures by ordering the initial molecular structures and the analogs of the initial molecular structures based on the determined scores; and updating parameters of the memory network based on a predefined number of highest-scoring molecular structures in the ordered list of molecular structures.

12. The method of claim 10, wherein the token string representations are SMILES representations or comprise 1-letter or 3-letter amino acid representations.

13. The method of claim 10, wherein sequentially processing the substructure token string representation of the substructure of the corresponding initial molecular structure comprises:

selecting a starting position in the corresponding initial molecular structure;

traversing the corresponding initial molecular structure from the starting position using a traversal rule to generate the token string representation of the corresponding initial molecular structure; and generating the substructure token string representation of the substructure of the corresponding initial molecular structure by taking a sequence of tokens from the token string representation of the corresponding initial molecular structure, wherein the sequence of tokens begins at a first token corresponding to the starting position.

14. The method of claim 10, wherein sequentially processing the substructure token string representation of the substructure of the corresponding initial molecular structure comprises:

selecting a starting position in the corresponding initial molecular structure;

traversing the corresponding initial molecular structure from the starting position for a plurality of steps using a traversal rule to generate a sequence of tokens corresponding to the substructure token string representations of the substructure of the corresponding initial molecular structure.

15. The method of claim 10, wherein the internal state of the memory network is updated after each token of the substructure token string representation of the substructure is read in; and wherein sampling one or more additional tokens using the memory network comprises updating the internal state of the memory network after each additional token is sampled.

16. The method of claim 10, further comprising:

generating a structure of one of the potentially biologically or medically active molecules; and synthesizing the potentially biologically or medically active molecule based on the generated structure.

17. One or more non-transitory computer readable media having instructions stored thereon which, when executed by a computing system, causes the computing system to perform operations for generating analogs of a molecule, the operations comprising:

receiving one or more initial molecular structures;

generating one or more token string representations for each of the one or more initial molecular structures, each token string representation corresponding to an analog of a corresponding initial molecular structure, wherein generating the one or more token string representations for each initial molecular structure comprises:

sequentially processing a substructure token string representation of a substructure of the corresponding initial molecular structure using a memory network, comprising sequentially reading the substructure token string representation of the substructure into the memory network for updating an internal state of the memory network; and subsequent to processing the substructure token string representation of the substructure, sampling one or more additional tokens using the memory network, wherein each of the one or more token string representations comprises a plurality of tokens representing predefined structures of a molecule, wherein the memory network encodes a sequential probability distribution on the plurality of tokens using the internal state of the memory network, and wherein the one or more additional tokens are sampled based on the sequential probability distribution.

18. The one or more non-transitory computer readable media of claim 17, wherein the operations for sequentially processing the substructure token string representation of the substructure of the corresponding initial molecular structure comprise:

selecting a starting position in the corresponding initial molecular structure;

traversing the corresponding initial molecular structure from the starting position using a traversal rule to generate the token string representation of the corresponding initial molecular structure; and generating the substructure token string representation of the substructure of the corresponding initial molecular structure by taking a sequence of tokens from the token string representation of the corresponding initial molecular structure, wherein the sequence of tokens begins at a first token corresponding to the starting position.

19. The one or more non-transitory computer readable media of claim 17, wherein the operations for sequentially processing the substructure token string representation of the substructure of the corresponding initial molecular structure comprise:

selecting a starting position in the corresponding initial molecular structure;

traversing the corresponding initial molecular structure from the starting position for a plurality of steps using a traversal rule to generate a sequence of tokens corresponding to the substructure token string representations of the substructure of the corresponding initial molecular structure.

20. The one or more non-transitory computer readable media of claim 17, wherein the internal state of the memory network is updated after each token of the substructure token string representation of the substructure is read in; and wherein sampling one or more additional tokens using the memory network comprises updating the internal state of the memory network after each additional token is sampled.

* * * * *